United States Patent [19]

Rounbehler et al.

[11] 4,249,904
[45] Feb. 10, 1981

[54] METHOD AND APPARATUS FOR EXTRACTION OF AIRBORNE N-NITROSO COMPOUNDS WITHOUT ARTIFACT FORMATION

[75] Inventors: David P. Rounbehler, Concord; John W. Reisch, Brookline, both of Mass.

[73] Assignee: Thermo Electron Corporation, Waltham, Mass.

[21] Appl. No.: 61,554

[22] Filed: Jul. 27, 1979

[51] Int. Cl.³ .................. G01N 31/00; G01N 27/62; C01G 28/00
[52] U.S. Cl. .................. 23/230 M; 23/232 R; 422/88; 55/70; 423/245; 252/436; 252/434; 252/428; 252/184
[58] Field of Search ............ 252/431 C, 438, 436, 252/430, 428, 184, 193; 423/245 S; 55/74, 70; 23/232 R, 232 C, 230 M, 232 E; 422/88, 89, 90–92, 52

[56] References Cited

U.S. PATENT DOCUMENTS

| | | | |
|---|---|---|---|
| 1,864,988 | 6/1932 | Downs | 252/428 |
| 2,140,271 | 12/1938 | Schwarcman | 252/436 |
| 2,237,459 | 4/1941 | Thompson | 252/436 |
| 2,694,923 | 11/1954 | Carpenter | 23/232 C |
| 3,996,002 | 12/1976 | Fire | 23/232 C |
| 4,003,257 | 1/1977 | Fletcher et al. | 73/23.1 |
| 4,131,544 | 12/1978 | Elani | 422/88 |

OTHER PUBLICATIONS

Russell, J. W., *Environmental Science and Technology*, vol. 9, No. 13, 1975, p. 1175.

Fire, D. H. et al., *Environmental Science and Technology*, vol. 11, No. 6, p. 577, 1977.

*Primary Examiner*—William F. Smith
*Assistant Examiner*—Chris Konkol
*Attorney, Agent, or Firm*—Herbert E. Messenger; James L. Neal

[57] ABSTRACT

A method and apparatus are disclosed for extracting N-nitroso compounds from air samples without artifact formation of nitrosamines from precursors in the sample. The apparatus includes a cartridge having two zones between a first port and a second port. The first zone, closest to the first port, contains an air pervious packing of a granular, solid phase amine complexing agent. The second zone, closest to the second port, contains an air pervious packing of a mixture of a granular, solid phase amine complexing agent and a particulate sorbent adapted to extract and concentrate N-nitroso compounds from air. The method includes a first step of driving an air sample through the first and second contiguous zones of the cartridge in succession, and a second step of driving an eluent through the second and first zones in succession, or backflushing the cartridge. To extract N-nitroso compounds, the eluent is a polar, or nitrogenous based, solvent for both N-nitroso compounds and the amine complexing agent in the second zone of the cartridge. The method may contain the further step of determining the N-nitroso compound concentration of at least a portion of the eluate which passes from the first zone following the second step of the method.

28 Claims, 8 Drawing Figures

METHOD AND APPARATUS FOR EXTRACTION OF AIRBORNE N-NITROSO COMPOUNDS WITHOUT ARTIFACT FORMATION

CROSS REFERENCE TO RELATED APPLICATIONS

This application is related to U.S. Patent Application Ser. No. 963,626, entitled "Method and Apparatus for Air Sampling and Filtration", filed Nov. 24, 1978, and issued Mar. 25, 1980, as U.S. Pat. No. 4,194,884 and to U.S. Patent Application Ser. No. 061,552, entitled "Method and Apparatus for Extracting Airborne Amine Compounds", filed on even date herewith. Those applications are incorporated by reference herein.

BACKGROUND OF THE INVENTION

This invention relates to air sampling systems and more particularly to methods and apparatus for removing N-nitroso compounds and amines from air samples and for providing quantitative analyses of the concentration of N-nitroso compounds in the air sample.

Devices and methods are known for sampling air to identify types and levels of organic compounds present in the environment. These compounds may arise from a variety of sources, such as the manufacture and use of chemicals, combustion of fuels, and others. Adsorbent materials are often employed in such devices to filter polluted air or trap measurable quantities of pollutants for analysis. While quantitative analyses of air are generally possible with such materials, the achievement of high sensitivity and consistent high accuracy has been difficult to obtain, particularly for the detection of complex organic compounds, such as nitrosamines, in low concentrations. One problem with use of adsorbent materials is that some adsorbents, such as activated charcoal, typically vary substantially in composition, and their adsorption characteristics, among manufacturers, and between batches from the same manufacturer. Also, many of the conventional adsorbent materials do not effectively trap certain low molecular weight compounds of interest. Even in cases where the compounds of interest are trapped, heat is commonly used to desorb the compounds from the adsorbent for analysis. This heat frequently results in the formation of additional amounts of the compounds whose detection is sought, or alteration of the trapped compounds. The use of certain "gas chromatographic" materials as adsorbents helps avoid variations in composition, but not the heat desorption problem. Moreover, the latter materials typically involve "breakthrough" problems, i.e. during trapping, certain of the compounds of interest gradually migrate through the gas chromatographic material in the direction of airflow and are lost from the collection device, leading to errors in the quantitative analysis. Certain other adsorbents, such as silica gel, may have at least one of the above-mentioned drawbacks. In addition, these other adsorbents exhibit an affinity for moisture which degrades their trapping efficiency and renders them unsuitable for analysis of moist air.

Among the substances whose detection in air and/or removal therefrom are of particular interest in the present invention, are N-nitroso compounds, each of which have the general formula:

where $R_1$ and $R_2$ are the same or different organic radicals including those radicals which together with the non-nitroso N of the depicted N-NO molecular bond constitute a nitrogen heterocyclic radial.

This group of compounds includes several nitrosamines which are known to be such potent carcinogens that dosages of a few parts per million have been observed to produce cancers in animals. The high carcinogenity of these compounds when inhaled or ingested has caused much concern regarding their occurrence in certain materials and in the environment.

In the continuing search for the presence of nitrosamines and their possible role in causing cancer in humans, considerable interest has developed in monitoring air, particularly in locations near factories and cities where volatile nitrosamines have been found and nonvolatile nitrosamines may also occur under certain conditions. However, accurate collection and analysis of samples from atmospheric environments is difficult in comparison to foods and chemicals, samples of which have readily been obtained for measurement of the content of nitrosamines. It is particularly difficult to achieve sufficiently rapid collection and analysis to adequately monitor air whose quality is susceptible to rapid change. Thus, it is important in such applications that the collection apparatus and techniques permit accurate and rapid analysis of the compounds extracted from the air. In addition, the technique and apparatus used to test air for the presence of N-nitroso compounds, whether or not part of a portable system, must permit trapping and retention of substantially all of the compounds in the air sampled.

Moreover, it is also known that nitrogen oxides (particularly $NO_2$, $N_2O_3$, and $N_2O_4$) can readily N-nitrosate precursor amines in gas phase reaction to form N-nitroso compounds. It is therefore possible that "detected" N-nitroso compounds may have been artifactually formed by N-nitrosation during the collection and analysis process. Consequently, an accurate air sampling and N-nitroso compound detection system must be effective in atmospheres in which precursor compounds are present in large concentrations.

According to one prior technique of detecting N-nitroso compounds in air, the air sample is bubbled through a dilute alkali impinger trap containing a 1 N solution of KOH (potassium hydroxide). The contents of the trap are then extracted using a solvent, dried and then concentrated. This extract is then analyzed for the presence of N-nitroso compounds. One major disadvantage of this method is that collection efficiency is low for certain N-nitroso compounds of interest such as N-nitrosodipropylamine, over 80 percent of which may pass through the bubble trap. Also, this method requires drying and concentration of the extract as by evaporation, which necessitates precise measurements and controls, is time consuming, and may introduce errors in the analysis.

According to another method which has been used to minitor air for N-nitroso compounds, air is drawn through cartridges containing a porous polymer of 2,6-diphenyl-p-phenylene oxide, such as Tenax GC available from Applied Science Laboratories, Inc., State College, Pennsylvania. This material traps the nitrosamines by adsorption. The trapped materials are desorbed using heat, then the desorbed materials are analyzed, for example, by capillary gas-liquid chromatography followed by low-resolution mass spectrometry. However, Tenax GC is relatively expensive. More importantly, the desorption by heat step after collection results in inaccuracies since the thermal desorption itself may produce nitrosamines from precursors, such as amines and compounds containing nitrogen and/or oxygen present in the cartridge, or may cause decomposition of some of the trapped N-nitroso compounds. Another deficiency of Tenax GC material is that it may not retain all of the N-nitroso compounds in the air pumped through the cartridge. The collection efficiency has been found in tests to be different for different N-nitroso compounds and after a certain volume of air has been drawn through the cartridge, further monitoring results in the "breakthrough" and loss of certain nitrosamines from the cartridge. The breakthrough volume of air is different for different N-nitroso compounds, being generally lowest for the smaller nitrosamines (such as N-nitrosodimethylamine) which are of maximum interest. These test techniques, as well as additional techniques using activated charcoal, and cryogenic traps, have been ineffective for nitrosamines with respect to artifact formation and collection efficiency.

Accordingly, it is a general object of this invention to provide improved methods and apparatus for removing predetermined organic compounds from air.

It is a more particular object of the invention to provide an improved method and apparatus for removing and determining the concentration of N-nitroso compounds in a sample of air.

It is another particular object of the invention to provide an improved method and apparatus for determining the concentration of N-nitroso compounds in an air sample without artifact formation of nitrosamines from precursors in the sample.

It is yet another object of the invention to provide an improved method for determining the content of predetermined organic compounds in a sample of air wherein the compounds may be trapped and then collected in a volume of solution sufficiently small so as not to require concentration of the solution during the determination.

It is also an object of the invention to provide apparatus for collecting organic compounds from air which is compact, inexpensive, portable, and simple to use.

SUMMARY OF THE INVENTION

The present invention is directed to methods and apparatus for extracting N-nitroso compounds and amines from an air sample without the formation of nitrosamine artifacts from precursors in the sample, and further determining the concentration of the extracted N-nitroso compounds in the sample. According to the invention, the extraction apparatus includes a cartridge having two zones between two ports. The first zone, closest to a first of the ports, includes an air pervious packing of a granular, solid-phase amine complexing agent, such as sulfamic acid.

The second zone, closest to the second of the ports, includes an air previous packing of a mixture of a granular solid-phase amine complexing agent and a particulate sorbent adapted to extract and concentrate N-nitroso compounds from air. In this second zone, the complexing agent may be the same as that in the first zone. The sorbent may be, for example, magnesium silicate in the form of finely-divided particles.

The cartridge may be used in conjunction with known analytical techniques, such as mass-spectroscopy, chromatography and selective pyrolysis, to provide accurate quantitative analysis of air samples.

In accordance with the method of the invention for extracting N-nitroso compounds, as a first step, an air sample may be injected at the first port of the cartridge, passed through the first and second zones in succession and out the second port. During this first step, the complexing agent in the first zone is effective to trap substantially all amines present in the air sample within that zone, thereby inhibiting N-nitrosation. As the air sample passes through the second zone, N-nitroso compounds in the air sample are substantially all adsorbed by the sorbent. In addition, a portion of the nitrogen oxides present in the sample become trapped in the second zone, with the remainder of the air sample passing out the second port.

Following the first step, the cartridge is backflushed by an eluent which is injected at the second port, and passed through the second zone and the first zone in succession, and out the first port. The eluent is selected to be a polar or nitrogenous based solvent for both N-nitroso compounds and the complexing agent in the second zone. By way of example, where the complexing agent in the second zone is sulfamic acid, a suitable eluent is acetone.

During this second step, as the eluent passes through the second zone, both the N-nitroso compounds and the amine complexing agent in that zone are dissolved. The dissolved amine complexing agent in the second zone interacts with the trapped oxides of nitrogen in that zone to render substantially all of these oxides of nitrogen unable to support N-nitrosation. By the time the eluent reaches the first zone, these oxides of nitrogen are no longer available to participate with amines trapped in that first zone in an N-nitrosation gas phase reaction and there can be substantially no artifact formation of N-nitroso compounds in the first zone.

Consequently, as the eluent emerges from the first port, that eluent contains only the N-nitroso compounds that had previously been trapped in the second zone, with substantially no artifacts formed from the precursor amines from the original air sample. This solution of the eluent and the N-nitroso compounds may then be collected as it emerges from the first port, and analyzed for nitrosamine content by pyrolysis followed by measurement of the amount of nitric oxide liberated.

It is an important feature of the air sampling apparatus and method of this invention that a simple, inexpensive, rapid sampling technique is provided for detection and measurement of low level N-nitroso compound concentrations. It is an additional important feature that with the invention, substantially all the nitrosamines from the sorbent are transferred to a relatively small volume of solution, thereby permitting use of simple analysis (by eliminating a requirement to concentrate the solution following collection and prior to analysis).

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
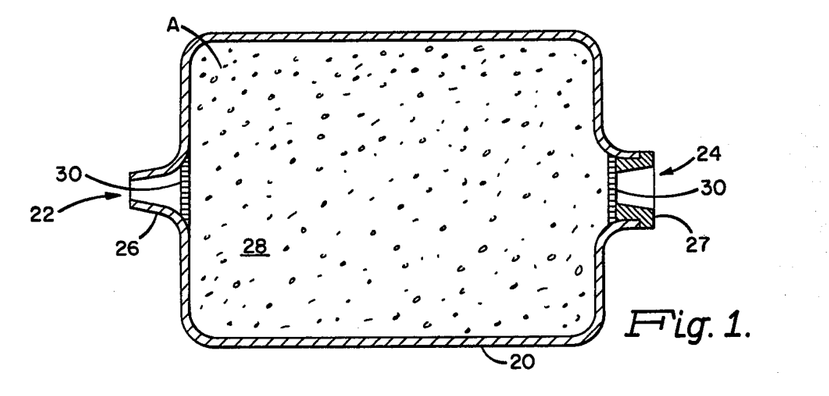
FIG. 1 shows in sectional view an N-nitroso compound collection device in accordance with the present invention.

FIG. 1 shows a sectional view of a cartridge 20 which may be used to separate nitrosamines from an air sample. Cartridge 20 is a thin-walled tube including a first port 22, a second port 24, and two zones (denoted A and B, and separated by broken line 25 in FIG. 1) between port 22 and port 24. Cartridge 20 is a polyethylene cylinder having a 15 mm inner diameter and a 20 mm depth. The port 24 includes a ring-shaped adapter 27 to permit the insertion of the tip of a syringe for injection a liquid phase eluent into the cartridge 20 through port 24. The walls 26 of port 22 are tapered away from the zones A and B to help direct the flow of the liquid phase eluent from the cartridge 20 during collection.

In the preferred embodiment, the cylindrical zone A has a depth of 6.7 mm and includes a packing 28 of a solid-phase, granular amine complexing agent (30-80 mesh, granular sulfamic acid). With this configuration, the packing 28 is pervious to the flow of air therethrough.

The cylindrical zone B has a depth of 13.3 mm and includes a packing 29 of a mixture of a solid-phase, granular amine complexing agent (30-80 mesh, granular sulfamic acid) (5%) and a particulate sorbent adapted to extract and concentrate nitrosamines from air (30-80 mesh, particulate magnesium silicate) (95%). The packing 29 too is pervious to the flow of air therethrough. One sorbent which has been tested and found to trap and hold N-nitroso compounds very effectively, is Florisil, a form of magnesium silicate manufactured by the Floridin Company of Warren, Pa. and sold by Fisher Scientific Company of Fair Lawn, N.J.

Stainless steel screens (100 mesh) 30 are positioned at the interior of ports 22 and 24 to hold packings 28 and 29 in place.

In operation, as a first step (FIG. 2), an air sample is drawn (by a pump, not shown) in succession through port 22, zone A, zone B and port 24. As a second step (FIG. 3), the pump is disconnected, and a liquid phase eluent is injected (e.g. by means of a syringe 40) into port 24, and passed in succession through zone B, zone A and port 22. At port 22, the eluate passes through a hollow needle (which ensures that the eluent does not "channel" in cartrdge 20, but rather wets all of packings 28 and 29). The eluent is a polar, or nitrogenous based, solvent for N-nitroso compounds and the amine complexing agent in zone B, or mixtures of such solvents. By way of example, acetone may be used as eluent.

After elution of selected compounds from cartridge 20, the solution is analyzed according to known techniques. One preferred method for measuring the N-nitroso compound content of a sample is set forth in U.S. Pat. No. 3,996,002, "Method and Apparatus for Measuring the N-Nitroso Compound of a Sample", issued to D. H. Fine, which disclosure is incorporated herein by reference. In this method, a liquid sample containing N-Nitroso compounds is non-catalytically pyrolyzed at a temperature in the range 300° C.–500° C. to break the N-NO bond in the N-nitroso compounds and liberate gaseous nitric oxide without breaking substantial numbers of other molecular bonds. Then, the amount of nitric oxide liberated is measured as by reacting the nitric oxide with ozine and sensing the intensity of the resulting chemiluminescent reaction. Since the presence of nitrates and nitrites trapped by and eluted from cartridge 20 might impair the accuracy of detection of nitrosamines, this measurement method preferably also includes a step prior to pyrolysis of the nitrosamines. According to this prior step, the nitrosamines are chromatographically separated from each other and from any nitrate or nitrite.

Among the N-nitroso compounds which may be removed for analysis according to this method are N-nitroso-dimethylamine, -diethylamine, -dipropylamine, -morpholine, pyrrolidine, -diethanolamine, -piperidine, -dibutylamine, -dihexylamine, -nornicotine, and -methylvinylamine. Cartridge 20 is particularly adapted for use as part of a sampling system for quantitative analysis of N-nitroso compounds in air samples.

During the first step described above, the amine complexing agent in packing 28 is effective to physically trap amines from the air sample as that sample passes through zone A. The dimensions of zone A and the packing density of the granular complexing agent are selected to both accommodate a desired air flow rate and ensure that substantially all such amines are trapped. As a result of this trapping, there is substantially no N-nitrosation in zone A as the input air sample passes through that zone.

The dimensions of zone B and the packing density of the mixture of th amine complexing agent and sorbent in packing 29 of zone B are selected to accommodate the desired air flow rate. In addition, the packing 29 composition and geometry is selected so that the sorbent is effective to trap substantially all (greater than 95%) of N-nitroso compounds passing in the air sample from zone A to zone B, and hold these compounds without loss during the entire monitoring interval, which may range from relatively short periods to several hours. Neither the complexing agent or the sorbent react chemically with the n-nitroso compounds trapped there nor do these materials combine with precursors to form nitrosmines.

In addition to separating and holding substantially all the nitrosamine without "breakthrough" and loss, the packing 29 is selected to readily release the N-nitroso compounds into the eluent injected through the cartridge 20 in the backflush step. It is important to note that the complexing agent in zone B is also soluble in the eluent and as a result, any oxide of nitrogen which may also be trapped in zone B interacts with the complexing agent, which is a known N-nitrosation inhibitor. As a result, when the eluent reaches zone A (which may include the trapped amine precursors of nitrosamine), there are no available oxides of nitrogen which may undergo N-nitrosation with those trapped amines. Consequently, there is substantially no artifact formation of nitrosamines in zone A, and the eluent which passes through the port 22 includes only the N-nitroso compounds from the original air sample.

In the present embodiment, sulfamic acid is used as the packing for zone A. However, in alternative embodiments, other granular, solid-phase amine complexing agents might be used, such as acids (particularly ascorbic acid) or ammonium sulfamate, for example. Moreover, the complexing agents in zones A and B may differ from each other. For example, zone A might include ascorbic acid, and zone B might include sulfamic acid, as the complexing agents.

The solvent or eluent employed to remove the N-nitroso compounds from sorbent material of mixture 29 is determined in part according to the polarity of compounds to be removed, and in part by the requirement that chemical reactions not occur between the eluent and either sorbent material of mixture 29 or compounds trapped thereby to form or alter any N-nitroso compounds, and, in addition, by the nature of the analytical techniques to be applid to measure the content of selected compounds removed from collection tube 20. In the present embodiment, the eluent is acetone. However, in alternative embodiments, ethanol, methanol, ammonia, pyridine, methyl cyanide, or pyrrolidine, or mixtures of any of these solvents or acetone may be used. Such mixtures may also be mixed with other solvents, such as dichloromethane (DCM). In still other embodiments, any polar, or nitrogenous based solvent, which is effective to dissolve both nitrosamines and the complexing agent, including water, may be utilized.

In the present embodiment, the sorbent utilized in zone B is magnesium silicate in the form of florisil. The sorbent may alternatively be selected from the group consisting of calcium silicate, activated charcoal, activated alumina, 2,6 diphenyl-p-phenylene oxide and alumina gel, or other sorbents which extract and concentrate N-nitroso compounds from air.

Figure 4:
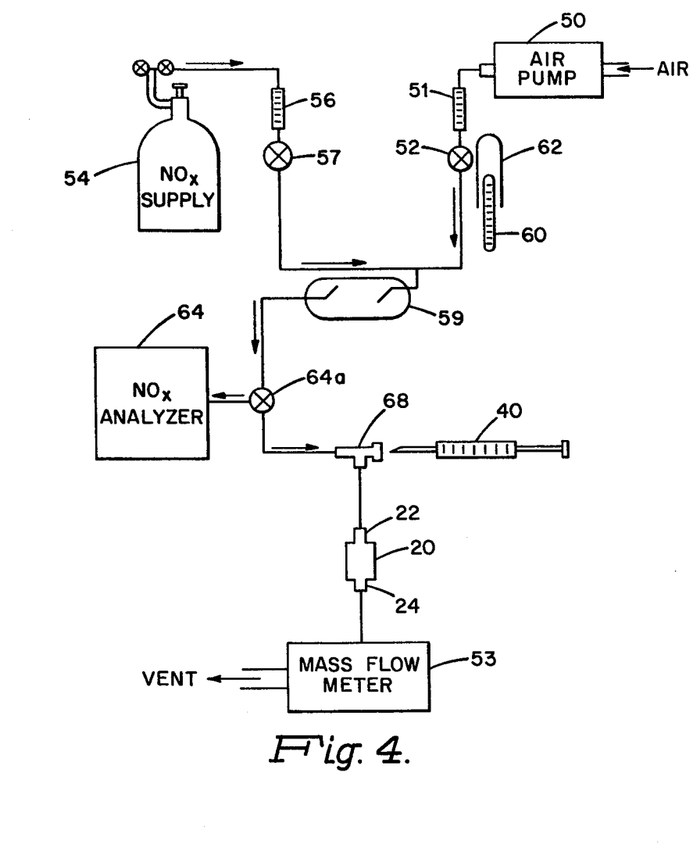
FIGS. 4 and 5 show in schematic configuration for testig the operation of the embodiment of FIG. 1.

FIG. 4 shows an exemplary test configuration for cartridge 20 described above. With this configuration, an air stream may be mixed with known quantities of oxides of nitrogen ($NO_x$), amines, and nitrosamines to simulate air samples from test environments. The resultant air stream is then passed through the cartridge 20 to extract the nitrosamines. In the illustrated test configuration, a constant flow of air (2 L/min) is provided by air pump 50 (e.g. 10 L/min metal bellows pump). The air stream is directed through a gas mixing apparatus controlled by a first rotameter 51 and control valve 52, and monitored by a mass flow meter 53 (Hastings, model ALL 10K). Known quantities of oxides of nitrogen gas are provided from a supply tank 54 by way of a second rotameter 56 and control valve 57. Tank 54 contains 1000 ppm NO and 73 ppm $NO_2$ in nitrogen. The air stream from pump 50 and the $NO_x$ from supply tank 54 are mixed in mixing chamber 59. Adjustment of the $NO/NO_2$ ratio in the gas stream may be accomplished in the line from pump 50 by generation of ozone with an ultraviolet lamp 60 equipped with a sliding cover 62. The concentration of NO and $NO_2$ in the mixed air stream may be monitored following mixing chamber 59 using the $NO_x$ Chemiluminescent Analyzer 64 (Thermo Electron, model 14B) and associated valve 64a. An injection port 68 is provided to permit injection of known quantities of nitrosamines and amines (by way of syringe 40) into the air stream prior to entry into the cartridge 20. The composite air stream (containing the air sample, $NO_x$, amines, and nitrosamines) is directed into port 22 of cartridge 20, through the cartridge, and out port 24, and then through mass flow meter 53 and vented.

Figure 5:
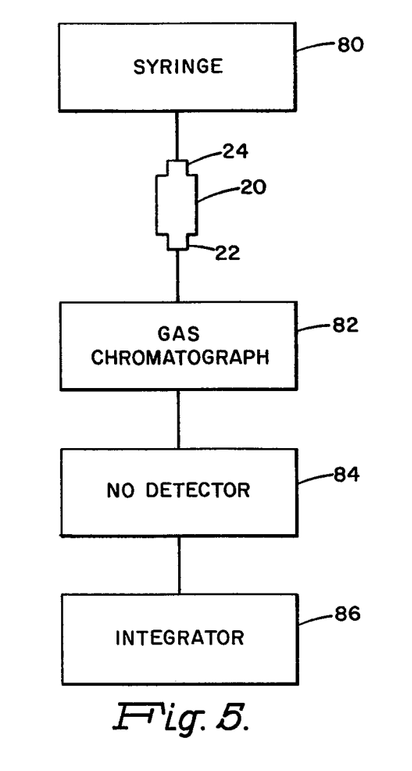

FIG. 5 shows an exemplary test configuration for analyzing the eluate passing from cartridge 20 following backflushing. In this configuration, a backflush (or eluent) syringe 80 is coupled to the port 24 of cartridge 20. The port 22 of cartridge 20 is coupled to a gas chromatograph 82 (Thermo Electron, model 661) interfaced to an NO detector 84 (Thermo Electron, model 502) for providing quantitative nitrosamine determinations. The gas chromatograph 82 is fitted with a 0.32 cm i.d $\times$ 500 cm stainless steel column packed with 5% Carbowax 20 M on Chromosorb W 100/120 mesh and is operated isothermally at 160° C. with argon as the carrier gas at 15 ml/min. An electronic integrator 86 (Hewlett/Packard, model 3880A) provides a comparison of chromatographic retention times to known standards.

To demonstrate the operation of the present invention, nitrosamines and amine test solutions were prepared by sequential volumetric dilution of the pure compounds. The nitrosamine test solution was made to contain 100 ug/ml in dichloromethane (DCM) of each of the following: N-nitrosodimethylamine (NDMA); N-nitrosodiethylamine (NDEA); N-nitroso-dipropylamine (NDPA); N-nitrosodibutylamine (NDBA); N-nitrosopiperidine (NPiP); N-nitrosopyrrolidine (NPYR) and N-nitrosomorpholine (NMOR). The amine test solution was made to contain 5000 ug/ml in DCM of each of the following: dimethylamine (DMA); di-n-isopropylamine (DIPA); piperidine (PIP); pyrrolidine (PYR) and morpholine (MOR).

Figure 6:
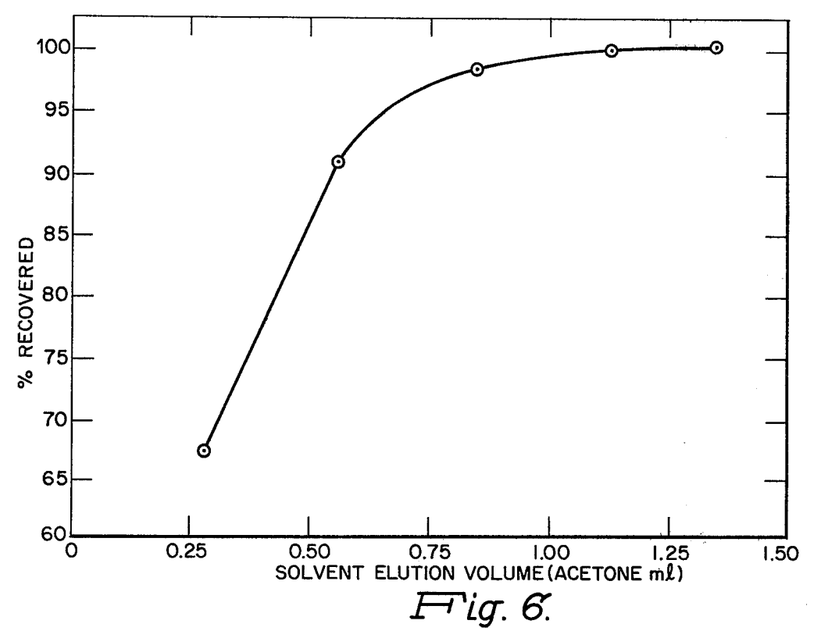
FIG. 6 shows the cumulative percent of nitrosamines recovered per milliliter of eluate for the embodiment of FIG. 1 under specific test conditions.

The efficiency of the cartridge 20 for adsorbing and de-adsorbing the test nitrosamines was initially determined. Using the configuration of FIG. 4, after pre-loading the cartridge 20 with 10 uL of the nitrosamine test solution, 100 liters of air were passed through the cartridge 20 at 2 L/min. Using the configuration of FIG. 5, the elution step was then performed by backflushing with acetone. The eluate was then analyzed by the chromatograph 82 and detector 84. FIG. 6 shows the cumulative percent of nitrosamines collected for each 0.25 ml of acetone-based eluate collected. As shown, substantially all of the nitrosamines were collected in the first milliliter of eluate.

Figure 7:
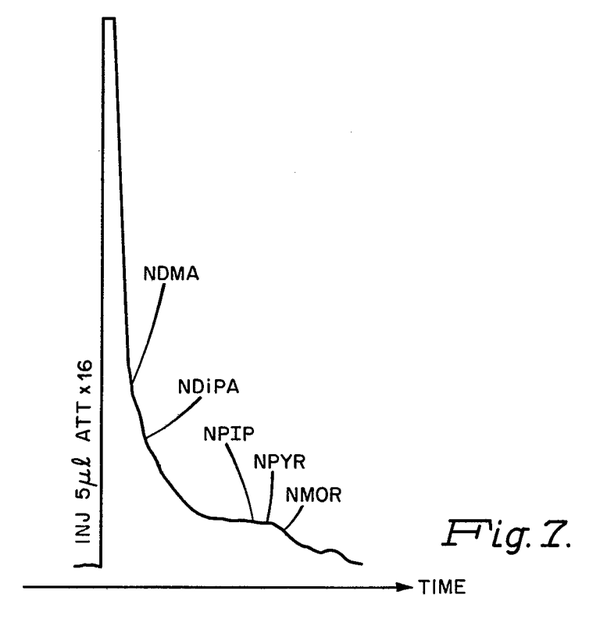
FIG. 7 is a chromatogram showing the suppression of N-nitrosamine artifact formation for the embodiment of FIG. 1 under specific test conditions.

To test for in situ nitrosamine artifact formation, the configurations of FIGS. 4 and 5 were used. With the FIG. 4 configuration, cartridge 20 was pre-loaded by injecting 10 uL of the amine test solution into a 2 L/min air stream and the allowing 10 minutes (20 L of air) to ensure that the added compounds were swept into cartridge 20. FIG. 7 shows the output chromatograph (from the GC-TEA analyzer 84 on the 16$\times$ Attenuation scale) showing zero detectable nitrosamines. After pre-loading with the five nitrosatable amines (at 50 ug each ), 100 liters of air containing 2 ppm NO and 2 ppm $NO_2$ were then injected into cartridge 20 by pump 50. With the test configuration of FIG. 5, the cartridge 20 was then backflushed with 2 ml of acetone to elute any nitrosamines which might have been formed (As shown in FIG. 6, substantially 100% of the nitrosamines are recovered in the first milliliter of eluate). The test configuration of FIG. 5 is characterized by a detection limit of 0.005 ug of nitrosamines. With this configuration, no nitrosamines were detected and thus nitrosamine artifact formation was below this level.

The linearity of cartridge 20 was measured using the configurations of FIGS. 4 and 5 wherein nitrosamines were pre-loaded in varying amounts from 25 ng to 1000 ng, and then eluted with 2 ml of acetone. In all cases, substantially all of the pre-loaded nitrosamines were recovered from the eluate.

In the above tests, the air flow rates, air sample volumes, air levels of nitrogen oxides and amount of added amines approximate conditions that have been encountered in sampling industrial environments for nitrosamines.

Figure 8:
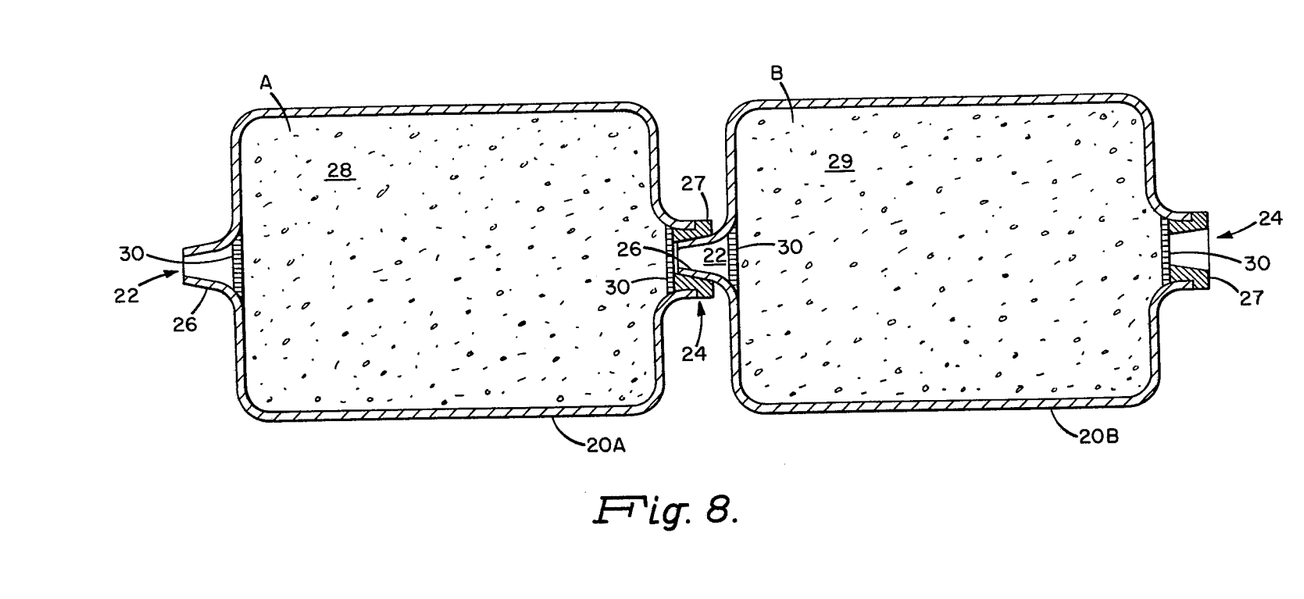
FIG. 8 shows in sectional view an alternate embodiment of the present invention.

In alternative embodiments, the present invention may be configured with zones A (and packing 28) and zone B (and packing 29) in separate but interconnected cartridges, such as shown in FIG. 8. In FIG. 8, elements which correspond to elements in FIG. 1 are identified by the same reference designations. In this configuration, a first cartridge 20A contains an air pervious packing of a granular solid-phase amine complexing agent, and a second cartridge 20B contains an air pervious packing of a mixture of a granular solid-phase amine complexing agent and a particulate sorbent adapted to extract and concentrate N-nitroso compounds from air. In this form of the invention, the cartridge 20A may have the same form as the cartridge 20 described in Patent Application Ser. No. 061,552, entitled Method and Apparatus for Extraction of Airborne Amine Compounds, filed on even date herewith, and incorporated by reference herein. Except for the use of separate cartridges for zones A and B, this form of the invention is substantially the same in both structure and method of operation as the cartridge described above in conjunction with FIGS. 1–3.

In all of the above-described forms of the invention, additional zones may be used in keeping with the present invention. More particularly, a drying zone (e.g. containing an air pervious packing of sodium sulfate or calcium carbonate) may be used between the first port and zone A. This zone would remove water from the air stream passed through the cartridge, but would not interfere with the operation of the invention otherwise.

In some uses of the invention, a wash step might be utilized between the step of passing the air sample through the cartridge and the backflushing step. This wash step might comprise passing a solvent for materials other than amines, nitrosamines, the complexing agents and sorbent through the cartridge to remove organic materials which might interfere with the subsequent analysis steps. By way of example for the preferred embodiment, a wash solvent such as hexane or pentane might be used to remove benzene.

While the above-disclosed embodiments of the present invention are particularly adapted for use as part of a sampling system for quantitative analysis of N-nitroso compounds in air, the essential principles of collection are applicable to air filtration and the cartridges may be readily modified for use in such devices as cigarette filters, gas masks, hoods for chemical apparatus, and various other air-conditioning apparatus.

Accordingly, the apparatus and method of the present invention have been demonstrated to efficiently collect N-nitroso compounds from an air sample without the artifact formation of nitrosamines from precursors in the sample, and also to determine concentrations of such compounds.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. Apparatus for extracting N-nitroso compounds from an air sample without artifact formation of nitrosamines from precursors in said sample, comprising:
    a cartridge having two interior zones between a first port and a second port,
    wherein the zone closest to said first port contains an air pervious packing of a first granular, solid-phase amine complexing agent, and
    wherein the zone closest to said second port contains an air pervious packing of a mixture of a second granular solid-phase amine complexing agent and a particulate sorbent adapted to extract and concentrate nitrosamines from air.

2. Apparatus according to claim 1 wherein said first and second complexing agents are acids.

3. Apparatus according to claim 1 wherein said first and second complexing agents are selected from the group consisting of sulfamic acid, ascorbic acid, and ammonium sulfamate.

4. Apparatus according to claim 3 wherein said first and second complexing agents are the same.

5. Apparatus according to claims 1 or 2 or 3 wherein said sorbent is a member of the group consisting of magnesium silicate, calcium silicate, activated alumina, activated charcoal, alumina gel and 2,6-diphenyl-p-phenylene oxide.

6. Apparatus according to claim 1 further comprising means for selectively driving an eluent through said zone closest to said second port and said zone closest to said first port in succession, said eluent being a polar or nitrogenous based solvent for nitrosamines and said second amine complexing agent.

7. Apparatus according to claim 6 further comprising means for selectively driving said sample through said zone closest to said first port and said zone closest to said second port in succession.

8. Method of extracting nitrosamine compounds from an air sample without forming nitrosamine artifacts from precursors in said sample, comprising the successive steps of:
    A. passing said sample through first and second zones of a cartridge in succession, said first zone containing an air pervious packing of a first granular, solid-phase amine complexing agent and said second zone containing an air pervious packing of a mixture of a second granular, solid-phase amine complexing agent and a particulate sorbent adapted to extract and concentrate nitrosamines from air,
    B. passing an eluent through said second and first zones in succession, said eluent being a polar, or nitrogenous based, solvent for nitrosamines and said second amine complexing agent, or mixtures of such solvents.

9. Method according to claim 8 comprising the further step following step B of collecting at least a portion of said eluent passing from said first zone, and determining the nitrosamine concentration of said portion.

10. Method according to claim 8 wherein said first and second complexing agents are acids.

11. Method according to claim 9 wherein said first and second complexing agents are selected from the group consisting of sulfamic acid, ascorbic acid, and ammonium sulfamate.

12. Method according to claim 11 wherein said first and second complexing agents are the same.

13. Method according to claims 9 or 10 or 11 wherein said sorbent is a member of the group consisting of magnesium silicate, calcium silicate, activated alumina, activated charcoal, alumina gel and 2,6-diphenyl-p-phenylene oxide.

14. Method according to claims 8 or 11 wherein said eluent includes one or a mixture of two or more members selected from the group consisting of acetone, ethanol, methanol, ammonia, pyridine, pyrrolidine, methyl cyanide and water.

15. Apparatus for extracting N-nitroso compounds from an air sample without artifact formation of nitrosamines from precursors in said sample, comprising:
- a first cartridge having an interior zone between a first port and a second port, and wherein said zone in said first cartridge contains an air previous packing of a mixture of a first granular solid-phase amine complexing agent and a particulate sorbent adapted to extract and concentrate nitrosamines from air;
- a second cartridge having an interior zone between a first port and a second port,
- means for coupling one port of said first cartridge to one port of said second cartridge, and
- wherein said zone in said second cartridge contains an air pervious packing of a second granular, solid-phase amine complexing agent.

16. Apparatus according to claim 15 wherein said first and second complexing agents are acids.

17. Apparatus according to claim 15 wherein said first and second complexing agents are selected from the group consisting of sulfamic acid, ascorbic acid, and ammonium sulfamate.

18. Apparatus according to claim 17 wherein said first and second complexing agents are the same.

19. Apparatus according to claims 15 or 16 wherein said sorbent is a member of the group consisting of magnesium silicate, calcium silicate, activated alumina, activated charcoal, alumina gel and 2,6-diphenyl-p-phenylene oxide.

20. Apparatus according to claim 15 further comprising means for selectively driving an eluent through said zone in said first cartridge and said zone in said second cartridge in succession, said eluent being a polar, or nitrogenous based, solvent for nitrosamines and said first amine complexing agent.

21. Apparatus according to claim 20 further comprising means for selectively driving said sample through said zone in said second cartridge and said zone in said first cartridge in succession.

22. Method of extracting nitrosamine compounds from an air sample without forming nitrosamine artifacts from precursors in said sample, comprising the successive steps of:
- A. passing said sample through a zone in a first cartridge and a zone in a second cartridge in succession, said zone of said first cartridge containing an air pervious packing of a first granular, solid-phase amine complexing agent and said zone of said second cartridge zone containing an air pervious packing of a mixture of a second granular, solid-phase amine complexing agent and a particulate sorbent adapted to extract and concentrate nitrosamine from air,
- B. passing an eluent through said zone of said second cartridge and said zone of said first cartridge in succession, said eluent being a polar, or nitrogenous based, solvent for nitrosamines and said second amine complexing agent, or mixtures of such solvents.

23. Method according to claim 22 comprising the further steps following step B of collecting at least a portion of said eluent passing from said first zone, and determining the nitrosamine concentration of said portion.

24. Method according to claim 22 wherein said first and second complexing agents are acids.

25. Method according to claim 22 wherein said first and second complexing agents are selected from the group consisting of sulfamic acid, ascorbic acid, and ammonium sulfamate.

26. Method according to claim 25 wherein said first and second complexing agents are the same.

27. Method according to claims 23 or 24 or 25 wherein said sorbent is a member of the group consisting of magnesium silicate, calcium silicate, activated alumina, activated charcoal, alumina gel and 2,6-diphenyl-p-phenylene oxide.

28. Method according to claims 22 or 25 wherein said eluent includes one or a mixture of two or more members selected from the group consisting of acetone, ethanol, methanol, ammonia, pyridine, pyrrolidine, methyl cyanide and water.

* * * * *

UNITED STATES PATENT AND TRADEMARK OFFICE
CERTIFICATE OF CORRECTION

PATENT NO. : 4,249,904
DATED : February 10, 1981
INVENTOR(S) : David P. Rounbehler et al.

Figure 2:
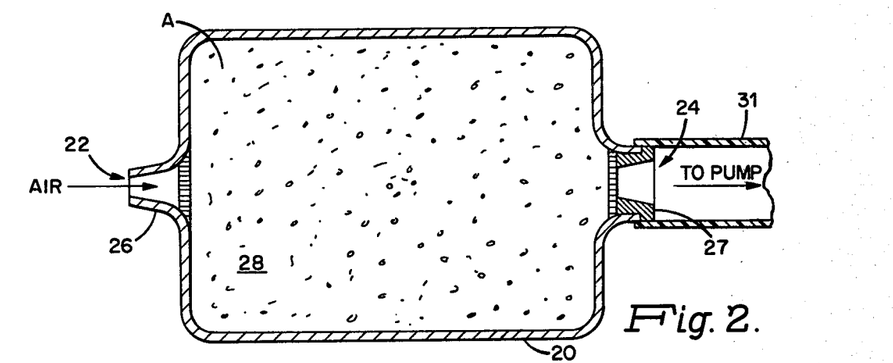
FIGS. 2 and 3 illustrate the method of the present invention as practiced with the embodiment of FIG. 1.
Figure 3:
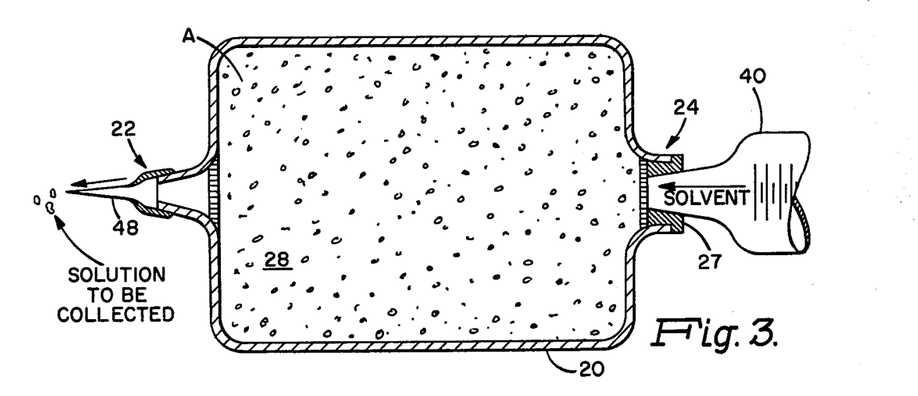

It is certified that error appears in the above—identified patent and that said Letters Patent is hereby corrected as shown below:

Figures 1, 2 and 3 should be cancelled and the attached sheet substituted therefor.

Signed and Sealed this

Sixteenth Day of June 1981

[SEAL]

Attest:

RENE D. TEGTMEYER

Attesting Officer     Acting Commissioner of Patents and Trademarks

Patent No. 4,249,904